United States Patent [19]

Thrower et al.

[11] Patent Number: 4,995,270

[45] Date of Patent: Feb. 26, 1991

[54] MOLTEN METAL SAMPLING

[75] Inventors: Anthony Thrower, Nr. Sheffield; Kenneth W. Bates, Chesterfield, both of England

[73] Assignee: Injectall Limited, Sheffield, England

[21] Appl. No.: 507,667

[22] Filed: Apr. 10, 1990

Related U.S. Application Data

[63] Continuation of Ser. No. 285,497, Dec. 29, 1988, abandoned.

[30] Foreign Application Priority Data

May 1, 1987 [GB] United Kingdom ............... 8710378

[51] Int. Cl.$^5$ .............................................. G01N 1/00
[52] U.S. Cl. ............................. 73/863.85; 73/DIG. 9
[58] Field of Search ........... 73/863.31, 863.81, 863.82, 73/863.85, 863.86, 864.51–864.59, DIG. 9; 266/99

[56] References Cited

U.S. PATENT DOCUMENTS

| | | | |
|---|---|---|---|
| 3,490,289 | 1/1970 | Mangin | 73/804.54 |
| 3,589,199 | 6/1971 | Levin | 73/425 |
| 3,915,014 | 10/1975 | Judge et al. | 73/864.54 |
| 4,125,024 | 11/1978 | Vierbicky | 73/425 |
| 4,290,306 | 9/1981 | Murakami et al. | 73/354 |
| 4,479,393 | 10/1984 | Shores | 73/863.86 |
| 4,575,393 | 3/1986 | Bates et al. | 75/53 |
| 4,624,149 | 11/1986 | Lawrenz et al. | 73/864 |
| 4,742,995 | 5/1988 | Bates | 266/270 |

FOREIGN PATENT DOCUMENTS

| | | | |
|---|---|---|---|
| 1533829 | 8/1971 | Fed. Rep. of Germany | 266/99 |
| 0222505 | 12/1984 | Japan | 266/99 |
| 1056214 | 3/1986 | Japan | 266/99 |
| 6616145 | 5/1967 | Netherlands | 73/863.81 |
| 301593 | of 0000 | U.S.S.R. | |
| 364183 | of 0000 | U.S.S.R. | |
| 585428 | of 0000 | U.S.S.R. | |
| 587358 | of 0000 | U.S.S.R. | |
| 634153 | of 0000 | U.S.S.R. | |
| 750321 | of 0000 | U.S.S.R. | |
| 2041182 | of 0000 | United Kingdom | |
| 2040750 | 9/1980 | United Kingdom | 73/864.52 |
| WO86/04928 | of 0000 | World Int. Prop. O. | |

OTHER PUBLICATIONS

"Ferrotron", Ferrotron Elektronik GmbH.

Primary Examiner—R. Raevis
Attorney, Agent, or Firm—Buchanan Ingersoll; Alvin E. Ring

[57] ABSTRACT

Apparatus and related method for taking a sample of molten metal from a vessel comprising a refractory block installed in a wall of the vessel before the vessel is filled with molten metal. The block is traversed by at least one passage having a closure element to initially block the passage. A rigid elongated pipe is movable lengthwise in the passage and a sample mould is operatively associated with the pipe. There is means activatable to advance the pipe forcibly in a forward direction to cause a forward end of the pipe to engage the closure element for unblocking the passage whereby molten metal gains access to the pipe and flows along the pipe to enter the mould.

35 Claims, 2 Drawing Sheets

MOLTEN METAL SAMPLING

This application is a continuation of application Ser. No. 285,497, filed Dec. 29, 1988, is now abandoned.

BACKGROUND OF THE INVENTION

The present invention relates to molten metal sampling, i.e. to a method and apparatus for extracting samples of metal from a bath of molten metal, for evaluation as by chemical analysis.

In the production of metals and alloys, it is frequently necessary to take samples of their melts for evaluation. Analyses, for example, are routinely performed to check on purity or constitution, so as to guide the metallurgist in taking corrective action. A particular need for evaluating melts routinely exists when continuously casting.

Commonly, samples for analysis are removed from a bath of molten metal by means of a lance which is lowered or plunged into the metal from above. The lance is plunged through the slag or flux layer and the sample taken by the lance could, therefore, be contaminated. Moreover, the use of a plunging lance may be restricted to taking samples from relatively shallow depths within the metal, so the samples obtained for evaluation may not be representative of the melt as a whole. Further, the lances are quite substantial and costly implements, have limited service lives and require quite elaborate equipment for manipulating them in the hostile environment above the molten metal bath.

FIELD OF INVENTION

The present invention seeks to provide a metal sampling method and apparatus which address some at least of the drawbacks of the conventional sampling technique outlined above.

According to the present invention, there is provided a method of taking a metal sample from a vessel of molten metal, comprising the steps of:

(a) before filling the vessel with metal, installing low in a wall of the vessel a refractory block having at least one passage therethrough extending from the exterior to the interior of the vessel, the said passage being closed or plugged at its interior end, (b) before or after filling the vessel with metal, inserting an elongated pipe into the or a passage therefor, the pipe having a sample mould operatively associated with an outer end thereof, (c) thrusting the pipe forcibly towards the vessel interior, to break or dislodge an element in said passage which closes or plugs the passage, and thereby to expose the pipe to the molten metal for the latter to run along the pipe and fill the mould, and (d) after allowing time for the metal that has accumulated in the mould to freeze or at least attain a pasty condition, separating the mould from the pipe thus obtaining a sample for evaluation.

The invention also provides a method of taking a metal sample from a vessel of molten metal, wherein the vessel has a refractory block installed low in a wall of the vessel, the block being traversed by at least one passage which extends from the exterior of the vessel to the interior thereof and is initially closed or plugged at its inner end, the method comprising inserting into the or a passage a pipe having at its outer end a sample mould, forcibly advancing the pipe at an element in the passage which closes or plugs the interior end, to break or dislodge the element and expose the pipe to the metal for the latter to run along the pipe and fill the mould and, after allowing time for the metal accumulated in the mould to freeze or at least attain a pasty condition, separating the mould from the pipe thus obtaining a sample for evaluation.

Beneficially, there is a plurality of initially-closed passages in the refractory block, thus enabling a plurality of samples to be taken at different times e.g. to monitor the course of corrective treatments that may be performed on the molten metal.

Advantageously, gas is injected into the metal to stir it before the pipe is forcibly advanced for collection of the sample, for instance from a location adjacent the passage by which the sample is to be taken. For example, the gas could be injected along another passage of the block via a gas pipe which is utilized to break or dislodge a closing element of that passage.

The invention comprehends a method of producing metal of a desired quality, purity or constitution, wherein (i) a sample of the metal is taken from a bath of melt thereof using the method defined hereinbefore, (ii) the sample is evaluated, (iii) thereafter the melt is treated in a manner indicated by the evaluated sample so as to render its quality, purity or constitution closer to what is desired, and (iv) steps (i) and (ii) at least are repeated, step (iii) being repeated if the evaluation of step (iv) shows further treatment is necessary.

Also according to the present invention, there is provided apparatus for use in taking a sample of metal from a vessel containing molten metal, comprising a refractory block for installing in a wall of the vessel, the block being traversed by at least one passage which has a frangible or dislogeable closure element therein, a rigid elongated pipe movable lengthwise in the passage, a sample mould operatively associated with the pipe, and means activatable to advance the pipe forcibly in a forward direction, in use to cause a forward end of the pipe to strike and break or dislodge the closure element, whereby molten metal gains access to the pipe and is free to flow along the pipe to enter the mould.

The invention also provides a sampler for use in this apparatus comprising a dispensible unit including a rigid, elongated pipe and a sample mould operatively associated with an end of the pipe, the mould being detachable from the pipe e.g. by the pipe being severable adjacent the mould after a metal sample has been collected in the sampler. Further, the invention provides a dipensible refractory body traversed by a plurality of passages all having frangible or dislodgeable closure elements located at one end of the body, and a plurality of samplers having pipes to fit movably in the passages the samplers being as defined in the last preceding paragraph.

BRIEF DESCRIPTION OF DRAWINGS

The invention will now be described by way of example only with reference to the accompanying drawing, the three Figures of which are longitudinal sectional views showing, in part, apparatus forming one embodiment of the apparatus. In the drawing.

DESCRIPTION OF PREFERRED EMBODIMENTS

Figure 1:
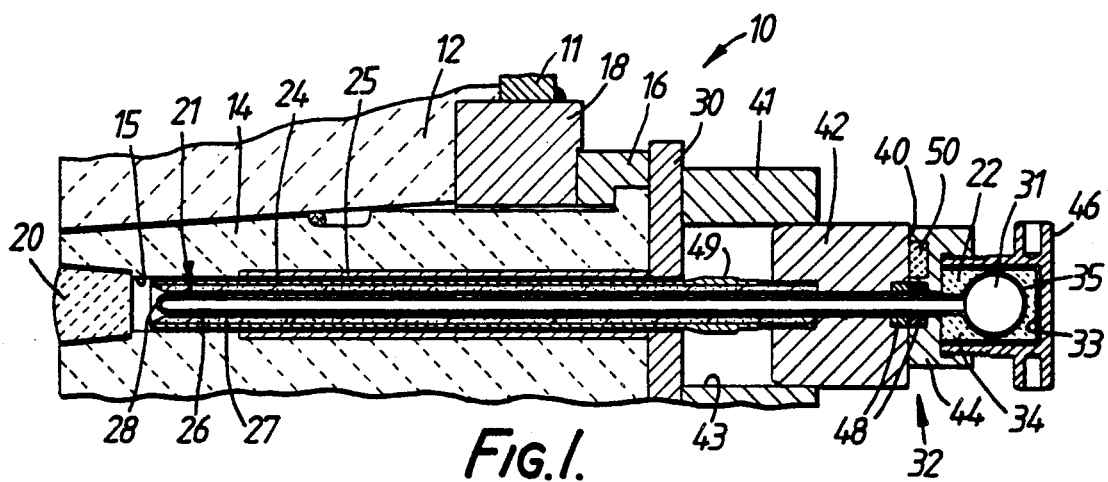
FIG. 1 shows the apparatus before taking a sample.

The apparatus 10 shown in the accompanying drawing is shown installed in an opening in the shell 11 and insulating lining 12 of a vessel such as a ladle for molten metal. The apparatus includes a dispensible and readily replaceable refractory body 14 which is pierced from end to end by at least one, and normally by a plurality of passages 15, e.g. eight or more. The refractory body 14 is cemented to the lining and is located properly with respect thereto by a locating ring 16 secured to an adaptor plate 18 which, in turn, is secured to the shell 11. The body 14 can be a pressed and fired refractory or, more economically, a castable cementitious refractory. The passages 15 are all closed initially, at their ends confronting the vessel interior, by closure elements such as plug 20. The closure elements may be frangible when struck. Alternatively the elements can be dislodgeably associated with their passages. As shown, the plug 20 is held in the end of the passage 15 by a layer of weak cement such that the plug can be expelled from the passage, into the vessel, when struck from within the passage.

The refractory body 14, with all passages 15 closed by plugs 20 is installed in the vessel wall before the vessel is filled with molten metal. It is located in a side of the vessel at a height dependent on the depth at which it is desired to acquire samples, well away from the surface of the melt and e.g. adjacent the bottom of the vessel.

Figure 2:
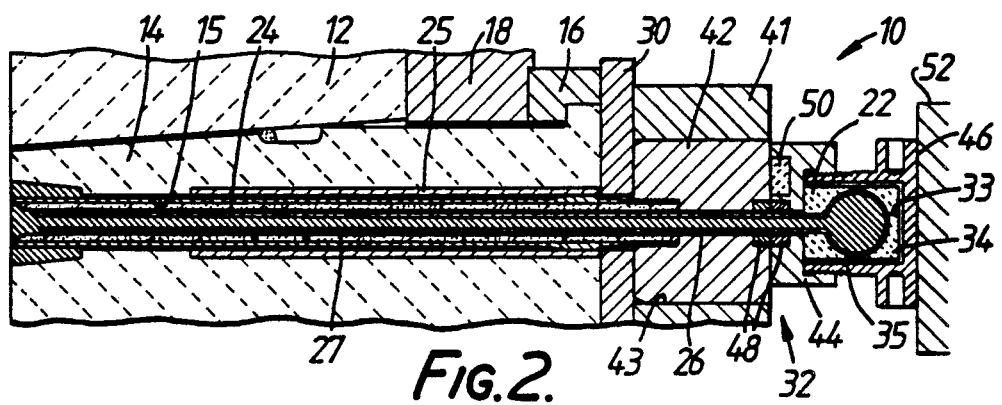
FIG. 2 shows the apparatus after taking a sample.

For taking samples, dispensible samplers have been devised. One such inventive sampler is shown. In essence, it comprises a pipe 21 operatively associated with a sample mould 22. The pipe 21 is guided for movement lengthwise in the passage 15, and is rigid and strong enough to withstand forces exerted thereon when an hydraulic or pneumatic actuator indicated at 52 in FIG. 2 is activated to thrust the sampler pipe at the plug 20 to dislodge same.

The pipe and mould can take several forms. The version shown will be described first, followed by alternatives.

The pipe 21 here comprises an elongated outer metal tube 24 having an outer diameter slightly smaller than the inner diameter of a tubular metal liner 25 in part defining the passage 15. A ceramic e.g. silica inner tube 26 is located coaxially inside the outer tube 24, and is affixed therein by cement 27. The inner tube 26 has an inlet end 28 set back slightly from the corresponding end of the outer tube 24 which, to initiate a sampling operation, has to strike and dislodge the plug 20. The two tubes project outwardly beyond the body 14 and through an orifice in a cover plate 30 which is secured to the ring 16. The inner tube 26 projects beyond the outer tube 24 and opens to the collection space 31 inside the mould 22. The outer tube 24 is screw threaded for attachment to part of a guide means 32 provided for supporting and guiding the sampler when actuated for taking a sample.

The mould 22 comprises a cup 33 filled with a refractory material 34. This can be a compressed refractory sand which may be bonded in known manner. The actual mould space in the refractory material can be defined in any convenient way, e.g. by a hollow mould member 35. The mould member can comprise a pair of mating half-shells made from glass, ceramic or pressed from thin metal, and can define a neck with which the inner tube 26 suitably interfits. The mould member 35 can be a spoon mould. The actual mould space can in principle have any chosen shape such as disc-shaped, lozenge-shaped or spherical by way of example.

The mould 22 per se could be a substantially commercially-available sample mould adapted by coupling it to the pipe 21 so that it is useable with the refractory body 14 for taking samples through the wall of a vessel without having to contend with the problems of entering the melt by passage through the slag or flux layer.

The inner tube 26 and mould member 35 could be formed integrally, for instance from a glass or ceramic material such as silica. The tube could be closed at its end 28 and the whole unit might be evacuated. The closed end must, however, be readily fusible when contacted by the molten metal, so that the latter can melt the end of the tube 26 and enter the sampler. A metal cap could be fitted and bonded to the end 28 of the tube 26, instead of the tube being necked and sealed.

It is not essential for the sampler to be evacuated and for the end 28 of the tube 26 to be closed. Molten metal will rapidly run into the tube 26 and to the mould space 31 thanks to the metallostatic head of the melt in the vessel. Air in the tube and space will be expelled from the latter if the mould member 35 is vented. Venting is assured if the mould member 35 comprises a split shell mould.

The outer tube 24 of the sampler pipe 21 need not be made of metal so long as it is strong enough to permit breaking or dislodging the closure or plug 20. It could, for example, be a ceramic tube.

As illustrated, the sampler pipe 21 comprises two coaxial tubes, cemented together. The cement could be omitted. The two tubes could be kept coaxial e.g. by appropriate resilient fastenings or spacers fitted at intervals along the pipe.

By appropriate changes of design, the sampler pipe 21 could consist of a single tube e.g. of metal, which will function (a) to break or dislodge the closure and (b) to convey melt to the mould 22.

Composite metal/ceramic tubes are known and such could be used as the sampler pipe 21.

As aforesaid, the mould space 31 is defined in the refractory 34 by a mould member 35 comprising a split-shell mould. It could, however, be a glass or ceramic bulb or the like. Still further, the mould member 35 could be omitted if the refractory 34 were bonded to retain the form of a suitably shaped moulding core. The mould space 31 could, therefore, be defined by known mould-forming methods.

The shape of the mould space 31 is basically immaterial and the shape illustrated is exemplary only.

By way of non-limiting example, the sampler pipe may provide a passage, along which the metal travels to the mould, some 5–10 mm in diameter and some 30 cm in length. The mould space may be of the order of 8–9 cc, e.g. 8.6 cc. In actual practice, these dimensions may be departed from substantially depending on the operating conditions.

The guide means 32 comprises a sampler holder 40 and location block 41, the latter being demountably attached to the cover plate 30. The holder 40 comprises three components. The first is a cylindrical body 42 which is telescopically movable in a location bore 43 in the block 41. The bore 43 is coaxial with the passage 15. The outer tube 24 of the sampler pipe 21 is screw threaded into a central hole in the body 42, while the inner tube 26 extends through a continuing bore in this body to a second body of the holder 40. The second body 44 is disposed face-to-face with the first body 42 and also has a bore therein, aligned with the bore in the first body 42. The inner tube 26 of the sampler pipe passes through this latter bore to the mould 22.

Mould 22 is located in a housing member 46, forming the third component of the holder 40. Member 46 has a hollow closely receiving the mould cup 33. The housing member 46 is screwed to the second body 44 of the holder 40.

The second body 44 is displaceably mounted to the first body 42. For example, the second body is guided by means, not shown, to slide downwards as viewed in the drawing. Alternatively, the second body is pivoted (by means not shown) about an axis offset from but parallel to the aligned bores of the two bodies 42, 44. The two bores at the interface between the confronting bodies 42, 44 are fitted with orificed shear discs 48. The shear discs are designed to sever the inner tube 26 and the metal therein, adjacent the mould, when a sample has been collected therein. Thus, the mould and sample can be removed for recovery and evaluation of the latter. Such severance is attained by displacing the second body, e.g. by a hydraulic ram, not shown. For advancing the sampler to cause the closure or plug 20 to be dislodged or broken, actuating means such as an hydraulic ram, not shown, acts on the holder 40 from the free end thereof, directly or via a suitable lever or linkage. The arrangement is such that the closure is disengaged from the passage when the holder body 42 has bottomed in the bore 43, at which time a sealing collar 49 on the outer tube 24 of the sampler pipe 21 has formed a melt-tight seal to the guide tube 25 in the refractory body 14.

Figure 3:
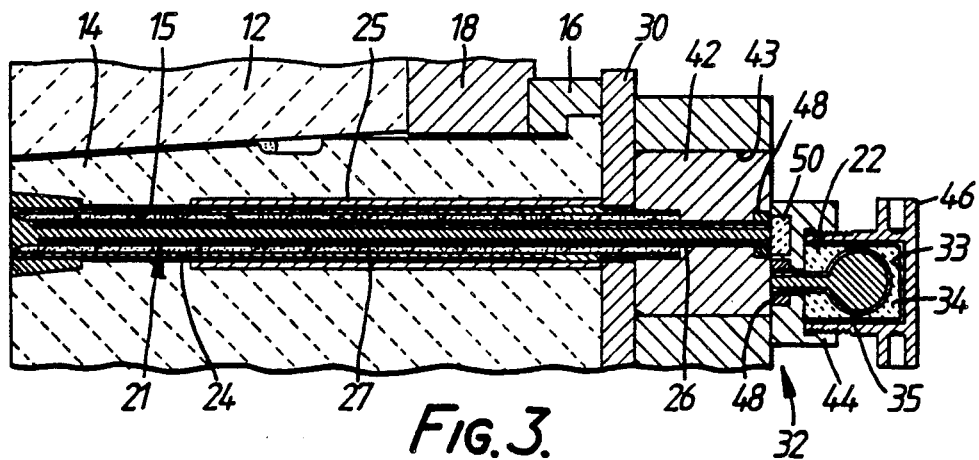
FIG. 3 shows the apparatus after taking a sample, and preparatory to removing the sample for evaluation.
Figure 4:
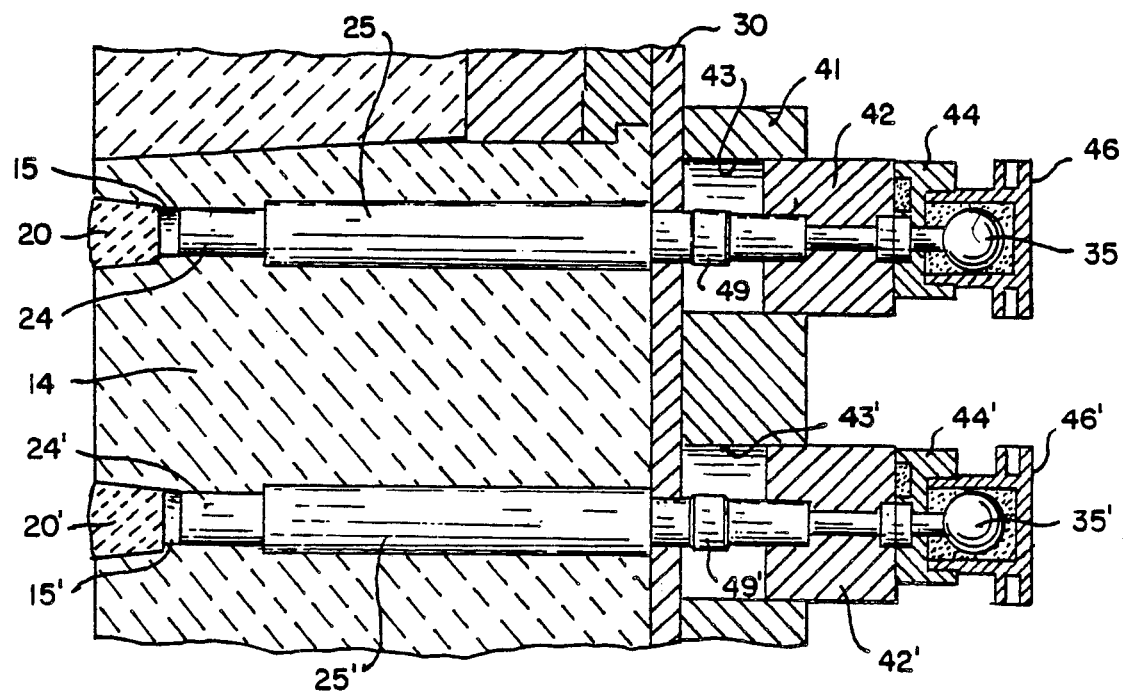
FIG. 4 shows an apparatus including a plurality of samplers.

When the second body 44 is displaced laterally relative to the first body of the holder 40, performing the shearing action, a seal disc 50 resistant to hot metal is placed across the end of the inner tube 26. See FIG. 3. The seal disc 50 is replaceably mounted in the second body 44 and serves a dual purpose—safety and protection of the body from damage by hot metal in the tube 26.

Ordinarily, the apparatus will permit a multiplicity of samples to be taken. For this purpose, the refractory body 14 possesses a plurality of initially-closed passages. A plurality of samples can thereby be obtained from each filling of the vessel. There may be sufficient passages to enable several samples to be taken from more than one filling of the vessel, so that the refractory body 14 will not need replacing each time the vessel is emptied. Whilst it is preferred for the apparatus to have a plurality of passages, apparatus within the invention may possess but one sampling passage.

In use, the body 14 is installed in the vessel wall with the aid of cement, and components 16 and 30 are secured to the mounting plate 18. The location block 41 is attached to the cover plate 30 and a sampler unit comprising the pipe 21 and mould 22 is inserted in the or a passage 15, the sampler unit having previously been assembled with the holder 40. The movable components comprising the sampler unit and holder 40 are set at a predetermined ready position by locating stop means, not shown, whereby the pipe 21 is close to, but safely spaced rearwardly of, the closure or plug 20. The ready position is indicated in FIG. 1.

To take a sample, the appropriate actuating means is energised to thrust the sampler unit towards the vessel interior, breaking or dislodging the closure element. The pipe 21 is thus exposed to the molten metal in the vessel, which will substantially instantaneously run along the pipe, via inner tube 26, and enter the mould space 31. See FIG. 2.

After allowing adequate time for the mould contents to freeze or at least attain a pasty i.e. substantially non-fluent condition, the mould is separated from the pipe. This is achieved by displacing the second body 44 of the holder 40, severing the inner pipe 26 and the metal strand therein at the interface between the holder bodies 42, 44. See FIG. 3. This done, the housing member 46 is unscrewed from the second body 44 enabling the mould 22 to be stripped therefrom. Thereafter the sample can be extracted from the mould 22, the cup 33 and refractory filling 34 being discarded.

When the closure is disengaged from the passage 15, melt will not only enter the pipe 21, but can also be expected to enter a clearance space between the pipe and the passage. It is expected that melt entering this clearance space will freeze, e.g. when it reaches the guide tube 25, effectively locking or welding the sampler pipe and tube 25 together. In the very unlikely event of the melt running back substantially the entire length of the guide tube 25, it will be arrested by the seal collar 49.

The freezing of the melt in the clearance space, coupled with its freezing in the inner tube 26 of sampler pipe 21, effectively safely closes the passage 15 against run out of melt once a sample has been taken.

The taking of other samples is performed as just described.

By use of apparatus having a plurality of passages, it is possible to perform a method of producing metal of a desired quality, purity or constitution, wherein (i) a sample of the metal is taken from a bath of melt thereof using the method just described, (ii) the sample is evaluated, (iii) thereafter the melt is treated in a manner indicated by the evaluated sample so as to render its quality, purity or constitution closer to what is desired, and (iv) steps (i) and (ii) at least are repeated using another sampler and passage, and step (iii) is repeated if the evaluation of step (iv) shows further treatment is necessary.

Beneficially, the melt is vigorously stirred immediately before a sample is taken, to ensure the latter is truly representative of the metal. This can be accomplished by injecting an inert gas into the melt. Injection of gas can be performed in various ways. It may be preferred for the gas injection site to be adjacent the sampling apparatus. For this purpose, one of the passages 15 in the plural-passage refractory body 14 could be utilised to inject gas. In principle, in the chosen gas passage a gas pipe instead of a sampler is installed, and the gas pipe is thrust forcibly at the closure or plug while the pipe is coupled to a suitably pressurized source of the gas. The gas pipe is thus employed to open its chosen passage to gas injection into the melt.

The method and apparatus herein described can be used for sampling substantially any metal or alloy such as may be produced in bulk in industry. Both ferrous and non-ferrous metals can be sampled safely, including very limpid melts such as molten iron.

INDUSTRIAL APPLICABILITY

The method and equipment disclosed herein are applicable to the sampling of molten metal contained in vessels such as ladles, for the purpose of inspecting or analysing the metal. The molten metal can be ferrous or non-ferrous, and by sampling and analysing the melt steps can be taken to modify its composition before the melt is poured from the vessel.

We claim:

1. A method of taking a metal sample from a vessel of molten metal, comprising the steps of:
    (a) before filling the vessel with metal, installing in a wall of the vessel of refractory block having at least one passage therethrough extending from the exterior to the interior of the vessel, said at least one passage being initially blocked,
    (b) before or after filling the vessel with metal inserting an elongated pipe into said at least one passage, the pipe having a sample mould operatively associated with an outer end thereof,
    (c) thrusting the pipe forcibly towards the vessel interior, to engage an element in said passage which initially blocks the passage, for unblocking the passage thereby to expose the pipe to the molten metal for the latter to run along the pipe and fill the mould, and
    (d) after allowing time for the metal that has accumulated in the mould to cool at least to attain a pasty condition, separating the mould from the pipe thus obtaining a sample for evaluation.

2. A method according to claim 1, wherein a gas is injected into the metal to stir it before the pipe is forcibly advanced for collection of the sample.

3. A method according to claim 2, wherein the gas is injected into the metal at a location adjacent the passage by which the sample is to be taken.

4. A method according to claim 3, wherein the gas is injected along another passage of the block via a gas pipe which is utilized to break or dislodge a closing element of that passage.

5. A method according to claim 1, wherein the pipe and mould form a sealed and evacuated unit and the unit has an end remote from the mould which is readily fusible when brought into contact with the metal, to allow the metal to enter the unit.

6. A method of producing metal of a desired quality, purity or constitution, wherein (i) a sample of the metal is taken from a bath of melt thereof using the method claimed in claim 1, (ii) the sample is evaluated, (iii) thereafter the melt is treated in a manner indicated by the evaluated sample so as to render its quality, purity or constitution closer to what is desired, and (iv) steps (i) and (ii) at least are repeated, step (iii) being repeated if the evaluation of step (iv) shows further treatment is necessary.

7. A method of taking a metal sample from a vessel of molten metal, wherein the vessel has a refractory block installed in a wall of the vessel, the block being traversed by at least one passage which extends from the exterior of the vessel to the interior thereof and is initially blocked, the method comprising inserting into said at least one passage a pipe having at its outer end a sample mould, forcibly advancing the pipe at an element in the passage which initially blocks said passage to unblock said passage and expose the pipe to the metal for the latter to run along the pipe and fill the mould and, after allowing time for the metal accumulated in the mould to attain at least a pasty condition, separating the mould from the pipe thus obtaining a sample for evaluation.

8. A method according to claim 7, wherein a gas is injected into the metal to stir it before the pipe is forcibly advanced for collection of the sample.

9. A method according to claim 8, wherein the gas is injected into the metal at a location adjacent the passage by which the sample is to be taken.

10. A method according to claim 9, wherein the gas is injected along another passage of the block via a gas pipe which is utilized to break or dislodge a closing element of that passage.

11. A method according to claim 7, wherein the pipe and mould form a sealed and evacuated unit and the unit has an end remote from the mould which is readily fusible when brought into contact with the metal, to allow the metal to enter the unit.

12. A method of producing metal of a desired quality, purity or constitution, wherein (i) a sample of the metal is taken from a bath of melt thereof using the method claimed in claim 7, (ii) the sample is evaluated, (iii) thereafter the melt is treated in a manner indicated by the evaluated sample so as to render its quality, purity or constitution closer to what is desired, and (iv) steps (i) and (ii) at least are repeated, step (iii) being repeated if the evaluation of step (iv) shows further treatment is necessary.

13. Apparatus for use in taking a sample of metal from a vessel containing molten metal, comprising a refractory block for installing in a wall of the vessel, the block being traversed by at least one passage, a closure element in said passage to initially block same, a rigid elongated pipe movable lengthwise in the passage, a sample mould operatively associated with the pipe, and means activatable to advance the pipe forcibly in a forward direction, in use to cause a forward end of the pipe to engage the closure element for unblocking said passage whereby molten metal gains access to the pipe and is free to flow along the pipe to enter the mould.

14. Apparatus according to claim 13, wherein the sample mould comprises a spoon mould with a neck to which the pipe is attached.

15. Apparatus according to claim 13, wherein the sample mould comprises a bulb-shaped cavity defined in a refractory mould body, a neck portion of the cavity being connected with the pipe.

16. Apparatus according to claim 13, wherein the mould is defined by mating parts of a metal, glass or ceramic shell.

17. Apparatus according to claim 13, wherein the pipe is closed at its forward end by means which are readily fusible upon contact with the molten metal.

18. Apparatus according to claim 13, wherein materials from which the pipe is made are selected from metals and ceramics.

19. Apparatus according to claim 13, wherein the pipe and mould comprise a sealed, evacuated unit.

20. Apparatus according to claim 13, wherein the pipe comprises a rigid outer tube and an inner tube communicating with the space inside the mould, the inner tube having its end remote from the mould closed and set back from the corresponding end of the outer tube, and said inner tube being made of materials selected from glass and ceramics.

21. Apparatus according to claim 13, wherein the pipe and mould are adapted to be severable adjacent the mould, for removal of the mould after collection of a sample therein.

22. Apparatus according to claim 13, wherein the pipe and mould constitute a one-use, dispensible unit.

23. Apparatus according to claim 13, wherein the advancing means includes a pneumatic or hydraulic actuator.

24. Apparatus according to claim 13, further including guide means for supporting the mould and an adjacent portion of the pipe and for guiding them when the advancing means is activated, the guide means including two bodies one of which is displaceable relative to the other and the bodies including means to sever the pipe upon displacement of the said one body, to enable removal of the mould and sample collected therein from the apparatus.

25. A sample for use in taking a sampler of metal from a vessel containing molten metal comprising a dispensible unit including a rigid, elongated pipe for extending into said vessel through the wall of said vessel and a sample mould for remaining outside the wall of said vessel operatively associated with an end of said pipe, the mould being detached from the pipe while the pipe remains in said wall after a metal sample has been collected in the sampler.

26. A sampler according to claim 25, wherein the pipe is severable adjacent the mould, to permit detachment of the mould therefrom.

27. A sampler according to claim 25, wherein said unit is sealed and evacuated.

28. A sampler according to claim 25, wherein the sample mould comprises a spoon mould with a neck to which the pipe is attached.

29. A sampler according to claim 25, wherein the sample mould comprises a bulb-shaped cavity defined in a refractory mould body, a neck portion of the cavity being connected with the pipe.

30. A sampler according to claim 25, wherein the mould is defined by mating parts of a shell mould.

31. A sampler according to claim 25, wherein the pipe is closed at its end remote from the mould by means which are readily fusible upon contact with the molten metal.

32. A sampler according to claim 25, wherein the pipe is made from materials selected from metals and ceramics.

33. A sampler according to claim 25, wherein the pipe comprises a rigid outer tube and an inner tube communicating with the space inside the mould, the inner tube having its end remote from the mould set back from the corresponding end of the outer tube, and the inner tube being made of materials which are selected from glass and ceramics.

34. A sampler according to claim 33, wherein the end of said inner tube remote from the mould is closed by means which are fusible when contacted by the melt.

35. A dispensable refractory body traversed by a plurality of passages all having frangible or dislodgeable closure elements located at one end of the body and a plurality of samplers having pipes to fit movably in the passages, each sampler having a mould attached to its pipe for collecting a sample, each mould being detachable from its pipe after collecting its sample.

* * * * *